(12) United States Patent
Armstrong

(10) Patent No.: US 7,277,570 B2
(45) Date of Patent: Oct. 2, 2007

(54) METHOD AND APPARATUS FOR WITNESS CARD STATISTICAL ANALYSIS USING IMAGE PROCESSING TECHNIQUES

(75) Inventor: Wayne Armstrong, Albuquerque, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 814 days.

(21) Appl. No.: 10/778,085

(22) Filed: Feb. 17, 2004

(65) Prior Publication Data

US 2005/0058334 A1    Mar. 17, 2005

Related U.S. Application Data

(60) Provisional application No. 60/502,623, filed on Sep. 15, 2003.

(51) Int. Cl.
G06K 9/00    (2006.01)
(52) U.S. Cl. .................. 382/141; 250/288; 250/423 P; 366/132; 427/8
(58) Field of Classification Search ............... 382/141, 382/103; 250/288, 423 P; 366/132, 160.2, 366/348; 118/679, 680, 683, 688, 692, 666; 427/8, 424, 427.5, 426, 427.2, 207.1, 427; 510/278, 302, 470, 530, 224, 446; 106/287.25, 106/287.26, 287.23
See application file for complete search history.

(56) References Cited

U.S. PATENT DOCUMENTS

| | | | | |
|---|---|---|---|---|
| 5,466,490 A | * | 11/1995 | Glancy et al. | ............... 427/422 |
| 5,509,959 A | * | 4/1996 | Nielsen et al. | ......... 106/287.35 |
| 6,072,890 A | * | 6/2000 | Savard et al. | ............... 382/110 |
| 6,266,437 B1 | * | 7/2001 | Eichel et al. | ............... 382/149 |
| 6,313,199 B1 | * | 11/2001 | Davies et al. | ............... 523/342 |
| 6,399,270 B1 | * | 6/2002 | Mori et al. | ............. 430/270.1 |
| 6,461,626 B1 | * | 10/2002 | Rabe et al. | ................. 424/401 |
| 6,950,547 B2 | * | 9/2005 | Floeder et al. | ............. 382/143 |

OTHER PUBLICATIONS

E. Franz et al., document No. 631445, "aerial spray deposit relations with plant canopy and weather parameters". Journal transactions of the ASAE, 1998, 41(4) pp. 959-966.*

(Continued)

Primary Examiner—Sheela Chawan
(74) Attorney, Agent, or Firm—Edell, Shapiro & Finnan, LLC

(57) ABSTRACT

A method and apparatus for performing witness card statistical analysis using image processing techniques to quickly and efficiently generate as-sprayed performance statistics for a spray device, or spray, based upon a comprehensive analysis of as-sprayed witness card stains. Calibration and as-sprayed witness cards are scanned to produce images that are processed using image processing techniques to identify stain areas/dimensions. Calibration stain data is associated with known calibration droplet volumes and used to generate a set of calibration equations that model an observed relationship between the area of calibration stains upon a witness card and the volume of the respective fluid droplets that produced the stains. As-sprayed stain area/dimension information is processed using the developed calibration equations to approximate the volume of as-sprayed droplets. The approach provides a direct quantitative assessment of spray device performance based upon a comprehensive assessment of as-sprayed witness cards, resulting in highly accurate, timely spray device performance statistics.

60 Claims, 4 Drawing Sheets

OTHER PUBLICATIONS

R.C.Derksen et al., document No. 631425, "automated detection of fluorescent spray deposits with a computer vision system", Journal transactions of the ASAE, 1995, vol. 38(6), pp. 1647-1653.*

H.Hurtig et al., diocument No. 631400, "a new technique for sampling and assessing aerial spray deposits". Canadian Journal of Agricultural science, vol. 36, Mar. 21, 1955, pp. 81-94.*

Sanderson et al: "Droplet Size Spectra of Dipel Sprayed Through Different Atomizers" Proceeding sof the Symposium of Pesticide Formulations and Application Systems, XP009041323, pp. 256-264.

Salyani, et al: "Performance of Image Analysis for Assessment of Simulated Spray Droplet Distribution" XP009041388, pp. 1083-1089.

* cited by examiner

METHOD AND APPARATUS FOR WITNESS CARD STATISTICAL ANALYSIS USING IMAGE PROCESSING TECHNIQUES

CROSS-REFERENCE TO RELATED APPLICATIONS

This application claims priority from U.S. Provisional Patent Application Ser. No. 60/502,623, entitled "Witness Card Image Processing" and filed Sep. 15, 2003. The disclosure of that provisional application is incorporated herein by reference in its entirety.

BACKGROUND OF THE INVENTION

1. Field of the Invention

The present invention pertains to performance analysis of instrument controlled spraying. In particular, the present invention pertains to the use of image processing techniques to determine as-sprayed drop statistics for sprayed witness cards (WC's).

2. Description of the Related Art

A wide variety of manufacturing and agricultural processes rely upon the use of instrument controlled spraying. For example, farmers and foresters typically use aircraft and/or farm equipment equipped with instrument sprayers to apply fertilizers and pesticides. Manufacturers use spray techniques to apply coatings and/or layers of a prescribed density and/thickness.

In the case of farming and forestry, the spraying process preferably results in a prescribed amount of fertilizer or pesticide being distributed uniformly to the ground, crop or trees. A spray that distributes too little fluid to a target area may reduce the effectiveness of the fertilizer or pesticide treatment, resulting in lost crops/trees and/or reduced yield. A spray that distributes too much fluid to a target area typically increases the cost of applying the treatment and may result in additional losses due to undesired side effects and/or pollution. A spray that distributes fluid to a target area unevenly, typically results in some portions of the sprayed area receiving too little treatment and other portions of the area receiving too much treatment, resulting in both types of losses described above.

Manufacturing environments, such as automobile production plant paint shops, plywood manufacturers, coated glass manufacturing, and other processing facilities typically used sprays to apply paint, adhesives, cleaning solutions, etc., at various steps of the production line. The ability to deliver a precise distribution of a sprayed solution in a specified period of time allows such plants to conserve resources, reduce waste, and to optimize a production line for consistent production.

In recent years, the ability to quantify the effectiveness of military and homeland security detection equipment designed to detect pollutants, toxic chemicals and/or biological agents within an environment has further increased the need for a fast and effective determination of spray characteristics as applied to a target area. For example, a laser interrogation system scans an operational environment to detect trace amounts of substances using Raman Spectrum based analysis. In order to perform operational testing of such a system, the precise nature of a sprayed distribution within the operational test must be precisely known.

The performance instruments used to dispense a fluid in the form of a mist, or spray, is typically quantified in terms of volume per unit time. This, plus sprayer motion results in a desired spray density and a mass median diameter (MMD) of droplets deposited upon a sprayed target. Spray density quantifies the number of droplets deposited within a predetermined area. Mass median diameter is the diameter for which one-half of the mass sprayed upon a target is contributed by particles smaller than the MMD and one-half of the sprayed mass is contributed by particles larger than the MMD. For example, if 1001 mg of solution is sprayed upon a target, the mass median diameter is the particle size such that 505.5 mg are contributed by particles smaller than the MMD and 505.5 mg are contributed by particles larger than the MMD. Assuming that each droplet is substantially spherical, measures of spray density and MMD provide a measure of the coverage achieved with the spray.

Currently, there is no reliable mechanism for setting an instrument controlled spraying device to deliver a precise spray of a selected fluid to a target. If droplets within a spray are too small, the droplets tend to drift away from their intended target, resulting in a low spray density and poor coverage. Larger droplets resist drifting, however, if the droplets are too large, a low spray density, and hence poor coverage, is again achieved. Further, the same control setting upon a spray device may result in a different as-sprayed result upon a target area due to a variety of external factors such as the temperature of the fluid being sprayed, the viscosity of the fluid at the current temperature, the distance of a target from the spray jet, the presence/absence of wind, high/low humidity, high/low ambient temperatures, and/or other factors which can cause portions of a spray to drift off and/or portions of the spray to evaporate prior to reaching a target.

The inability to control such spray characteristics via a spraying device, especially with respect to agricultural, forestry and military test operations, in which fluids are typically sprayed from aircraft and/or ground vehicles operating in relatively uncontrolled environments, requires that a spray's characteristics be sampled/monitored within a sprayed area in order to determine the spray characteristics achieved by a specific sprayed application. Such sampling/monitoring is also helpful in controlled environments such as production lines to periodically ascertain the as-is characteristics of an applied spray.

Typically, such monitoring is performed by laying down paper or cardboard cards, commonly referred to as witness cards, at one or more locations within an area to which a spray is to be applied. The witness cards absorb the sprayed drops resulting in a fixed pattern of stains of varying sizes deposited on the cards. Thus, each card captures a representative sample of the spray at a location within the sprayed area. Once stained, a witness card is analyzed and the stain pattern is translated into a characterization of the spray in terms of spray density, MMD and other statistical parameters.

Unfortunately, conventional techniques for processing witness cards are quite limited. For example, one technique is to take pictures of small portions/samples of a witness card and to manually assess the droplet stains found within each successive sample. A single witness card is typically sampled until a maximum of 15 portions/samples are processed or until information on 100 droplets is collected. Information related to the droplet stains is used to characterize the spray at the location of the witness card. By collecting information related to multiple witness cards distributed over an area subjected to a spraying operation, statistics related to the overall spraying are generated.

The above process is typically performed manually, with visual aids. Assessment of fifteen witness card portions/samples or 100 spots per card have conventionally been considered sufficient to statistically characterize the spraying operation with respect to the witness card. However, despite the use of such statistical methods, the process typically takes several weeks to complete. During that time, an individual selects and processes portions/samples on each witness card and feeds the collected witness card stain analysis information into a computer that computes a spray density and MMD for the spray. Such an approach is susceptible to significant variation due to the possibility of human error with respect to the witness card portion/sample areas selected for assessment and human error with respect to determining the diameters of the identified stains.

Hence, a need remains for a method and apparatus that allows the performance of a spray device to be quickly and accurately assessed. Preferably, such an approach would provide a direct quantitative assessment of spray device performance based upon an assessment of a greater number of available spray droplets rather than relying upon sampling techniques, thus avoiding human judgment error associated with current sampling techniques. Further, the spray performance analysis would preferably be capable of being performed by technicians without specialized experience or special stain analysis knowledge and/or training.

OBJECTS AND SUMMARY OF THE INVENTION

Therefore, in light of the above, and for other reasons that may become apparent when the invention is fully described, an object of the present invention is to collect accurate spray performance data.

Another object of the present invention is to reduce the time, or analysis delay, required to produce accurate spray performance data.

Yet another object of the present invention is to eliminate human error and/or the introduction of human bias in spray performance data collection and assessment.

Still another object of the present invention is to reduce the level of expert knowledge needed by a technician to generate accurate and timely spray performance data.

A further object of the present invention is to improve the consistency and reliability of spray performance analysis.

Yet a further object is to increase the number of WC stains analyzed during the spray performance analysis process by several orders of magnitude, and to perform the processing in near real time.

A still further object of the present invention is to increase spray performance analysis options to accommodate a wide variety of spray conditions and/or applied uses for spray performance analysis data.

The aforesaid objects are achieved individually and in combination, and it is not intended that the present invention be construed as requiring two or more of the objects to be combined unless expressly required by the claims attached hereto.

Method and apparatus are described for performing witness card statistical analysis using image processing techniques to quickly and efficiently generate as-sprayed performance statistics for a spray device, or spray, based upon a comprehensive analysis of as-sprayed witness card stains. Calibration and as-sprayed witness cards are scanned to produce images that are processed using image processing techniques to identify stain areas/dimensions. Calibration stain data is associated with known calibration droplet volumes and used to generate a set of calibration equations that model an observed relationship between the area of calibration stains upon a witness card and the volume of the respective fluid droplets that produced the stains. As-sprayed stain area/dimension information is processed using the developed calibration equations to approximate the volume of as-sprayed droplets. The approach provides a direct quantitative assessment of spray device performance based upon a comprehensive assessment of as-sprayed witness cards, resulting in highly accurate, timely spray device performance statistics.

The above and still further objects, features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION OF THE PREFERRED EMBODIMENTS

The use of witness cards to assess spray device performance is based upon the observed knowledge that dimensions of a stain produced upon a witness card by a drop of fluid can be correlated to the volume of the drop of fluid that produced the stain. As described above, however, correlation of stain dimensions to droplet volume can be affected by many factors, including the current temperature of the fluid, viscosity of the fluid at the current temperature, absorption properties of the card stock, the visual clarity of the resulting stain, etc. Further, given the large number of stains typically generated by a spray, unless a large percentage of the witness card stains are evaluated in performing the assessment, the performance characteristics of the spray device (e.g., spray density and MMD) may be miscalculated. To overcome the limitations of conventional techniques for analyzing stained witness cards to assess spray device performance, the present invention integrates witness card scanning, modern image analysis, witness card calibration and statistics generation into a single automated system.

Figure 1:
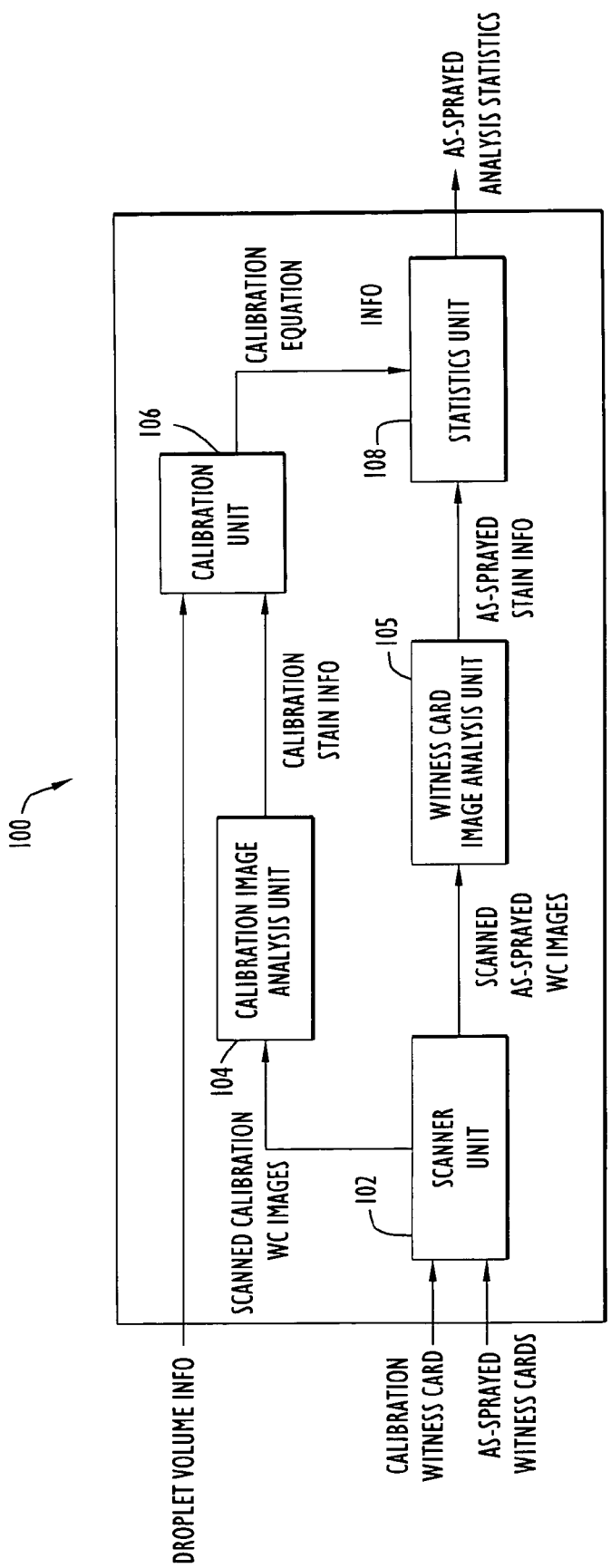
FIG. 1 is a block diagram of a spray performance analysis system in accordance with an exemplary embodiment of the present invention.
Figure 2A:
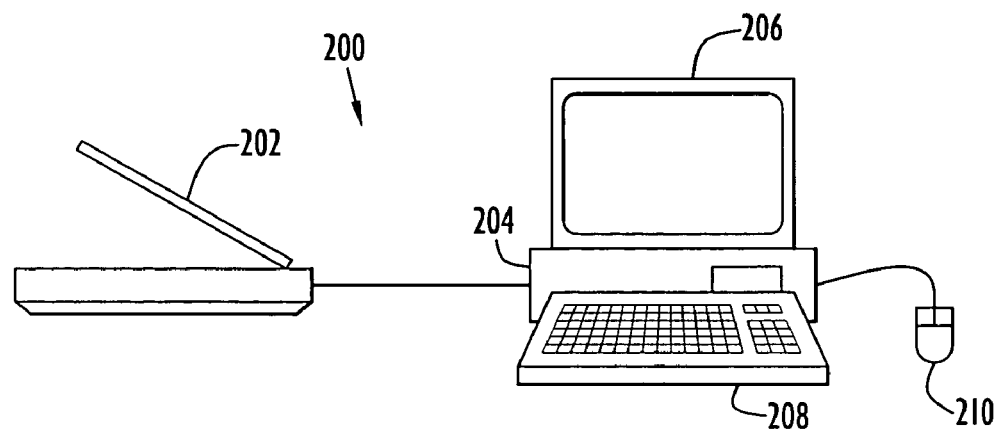
FIGS. 2A and 2B are schematic diagrams of stand-alone and networked computer environments, respectively, capable of supporting a spray performance analysis system in accordance with an exemplary embodiment of the present invention.
Figure 2B:
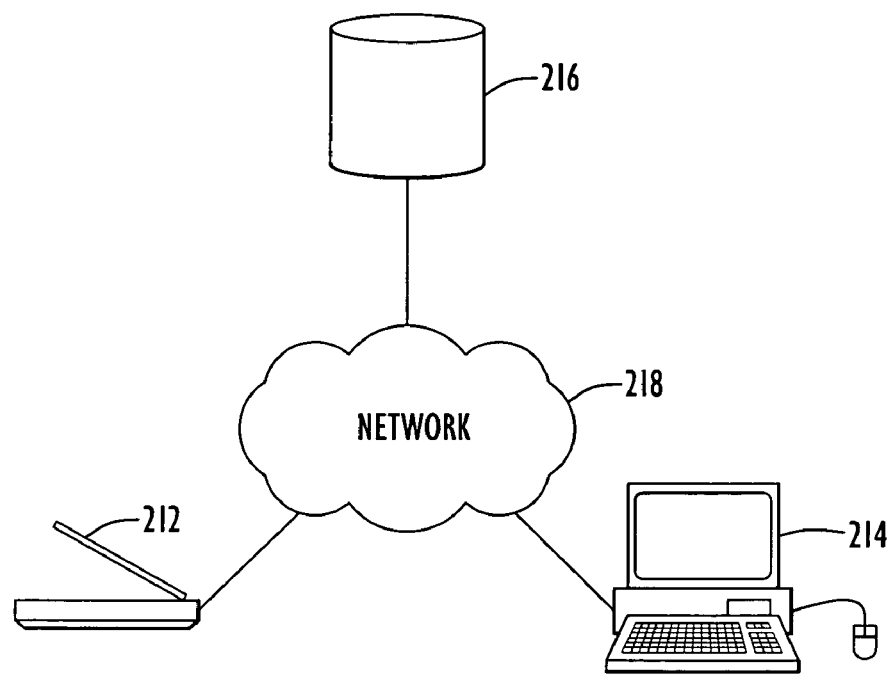

FIG. 1 is a block diagram of a spray performance analysis system 100 in accordance with an exemplary embodiment of the present invention. As shown in FIG. 1, analysis system 100 includes a scanner unit 102, a calibration image analysis unit 104, a WC image analysis unit 105, a calibration unit 106 and a statistics unit 108. Scanner unit 102 scans witness cards to produce witness card images that are submitted to either unit 104 or unit 105 depending on the type of image being processed. Scanned images of calibration witness cards are submitted to unit 104. Scanned images of as-sprayed witness cards are submitted to unit 105. The image analysis units 104 and 105 preferably include the same core image preprocessing control parameters, but are configured to perform different functions. The calibration image analysis unit 104 generates stain area information from calibrated drops of one, or several stains as directed by the user. The WC image analysis unit 105 automatically identifies as many as all of the stains within a witness card image and may determine stain areas for each identified stain and physical attributes of the stain image space. Calibration unit 106, receives calibration witness card stain dimension data from calibration image analysis unit 104 and known droplet volume information to generate a calibration curve equation, or set of linear and/or non-linear equations, capable of accurately estimating a droplet dimension (e.g., droplet diameter or MMD) as a function of a determined stain dimension (e.g., stain diameter) for an identified fluid at an identified temperature upon an identified paper stock. Statistics unit 108 receives and stores one or more calibration equations generated by calibration unit 106. Upon receiving as-sprayed witness card stain dimension data from WC image analysis unit 105, statistics unit 108 may select a stored calibration equation, or set of equations, based upon the fluid, fluid temperature and paper stock used to produce the as-sprayed stains. Statistics unit 108 then uses the selected calibration equation(s) to estimate spray droplet diameters (i.e., MMD values) and spray density for each as-sprayed witness card. In addition, based upon the number of droplets, spray density and MMD values determined for each as-sprayed witness card retrieved from a known location within a sprayed target area, statistics unit 108 is capable of generating statistical data that characterizes spray performance within any or all portions of the sprayed target area.

The spray performance analysis system described here can be implemented in any number of units, or modules, and is not limited to any specific software module or hardware architecture. Each module can be implemented in any number of ways and are not limited in implementation to execute process flows precisely as described above. The spray performance analysis system described above and illustrated in the flow charts and diagrams may be modified in any manner that accomplishes the functions described herein. It is to be understood that various functions of the spray performance analysis system may be distributed in any manner among any quantity (e.g., one or more) of hardware and/or software modules or units, computer or processing systems or circuitry.

FIG. 2A presents an exemplary embodiment of the present invention in which a spray performance analysis system 200 is implemented in a stand-alone configuration. As shown in FIG. 2A, such an embodiment may include a scanner 202, and a conventional computer processing unit 204 with conventional user input/output devices such as a display 206, keyboard 208 and mouse 210. The computer system may use any of the major platforms such as Windows, Linux, Macintosh, Unix or OS2. Further, computer processing unit 204 includes components (e.g. processor, disk storage or hard drive, etc.) having sufficient processing and storage capabilities to effectively execute spray performance analysis system processes. In such an embodiment, a user interfaces with the spray performance analysis system executing upon computer processing unit 204 via a command line or graphical user interface to scan and process witness cards in accordance with the present invention. Scanning, image analysis, generation of calibration equations, and the generation of as-sprayed statistics is performed from a single location.

FIG. 2B presents an alternate exemplary embodiment of the present invention in which spray performance analysis system functions are performed in a distributed networked environment. As shown in FIG. 2B, a scanner 212, computer processing unit 214 and storage device 216 are connected by communication network 218. In such an environment, scanner 212 is typically used to generate scanned images of calibration witness cards and/or as-sprayed witness cards and to store the scanned images to networked storage device 216. In this manner, scanned images can be generated, stored and later retrieved by processing unit 214 in order to develop calibration equations and/or generate as-sprayed analysis statistics.

Paper stock used as witness cards by the spray performance analysis system of the present invention is preferably selected to avoid paper speckle (i.e., single or small clusters of pixels within a witness card image caused by the grain and/or structure of the paper stock) and to avoid paper imperfections (i.e., larger groups of pixels caused by paper stock local area imperfections or lack of homogeneity in the grain structure of the paper). Unless paper speckle and paper imperfections are avoided in the selected paper stock, the resulting distortions within stained witness card images may introduce significant error in calibration equations and as-sprayed drop statistics generated by the spray performance analysis system. One commercially available stocks of paper that demonstrates consistently low paper speckle and paper imperfections, and which is therefore a preferred source of witness card paper stock is sold as Epson 52 lb., single side glossy photo paper, stock number S041649. It is further preferred that the paper stock used to calibrate the spray performance analysis system for a selected fluid and the paper stock used in the as-sprayed witness cards originate from a commonly manufactured batch of the preferred paper stock.

The temperature of a sprayed fluid can have significant effects upon the diameter of stains produced upon a witness card by droplets of the sprayed fluid. For example, data collected with respect to the effects of temperature upon drop stain diameters for the fluid thickened Methyl Salicylate (TmeS) indicates a change in stain diameter of approximately negative one-half percent (−0.5%) per degree Fahrenheit of the TMeS fluid above ambient temperature.

The viscosity of a sprayed fluid can also have significant effects upon the diameter of stains produced upon a witness card by droplets of the sprayed fluid. For example, assessment of data related to TMeS droplets indicates that stain diameters produced by TMeS droplets of known drop mass may change significantly in response to a change in viscosity of negative 40% from 831 Cp, or 504.6 Cp. Further, the assessment of TMeS data indicates that the changes in stain diameters due to changes in fluid viscosity may vary for different sized droplets. For example, droplets less than 0.15 mg demonstrate increases in stain diameter between 0% and 2.5%, while droplets greater than 0.15 mg demonstrate drops in stain diameter between 0% and 1%.

The examples above address observed changes with respect to the stain diameter created by droplets of a single fluid compound as the result of changes with respect to only two fluid characteristics (i.e., temperature and viscosity of the sprayed fluid). When performing as-sprayed performance testing under operational conditions, however, the stain diameter created by a sprayed fluid droplet upon a witness card may be affected by the interaction of numerous physical factors. Such factors may include slight variations in the composition of the sprayed fluid, varying rates of evaporation into the ambient atmosphere for different fluid/ambient environment temperature levels and/or temperature differentials, varying surface tension/viscosity characteristics of various sized droplets of the sprayed fluid at different temperatures and the absorption/wicking characteristics of the selected witness card stock in response to the various sized droplets of the sprayed fluid. Given the large number of factors that can affect witness card stain dimensions, witness card calibration is preferably performed for each as-sprayed test, using the same sprayed fluid compound at the same temperature and under the same operational conditions under which the as-sprayed witness cards are produced.

Figure 3:
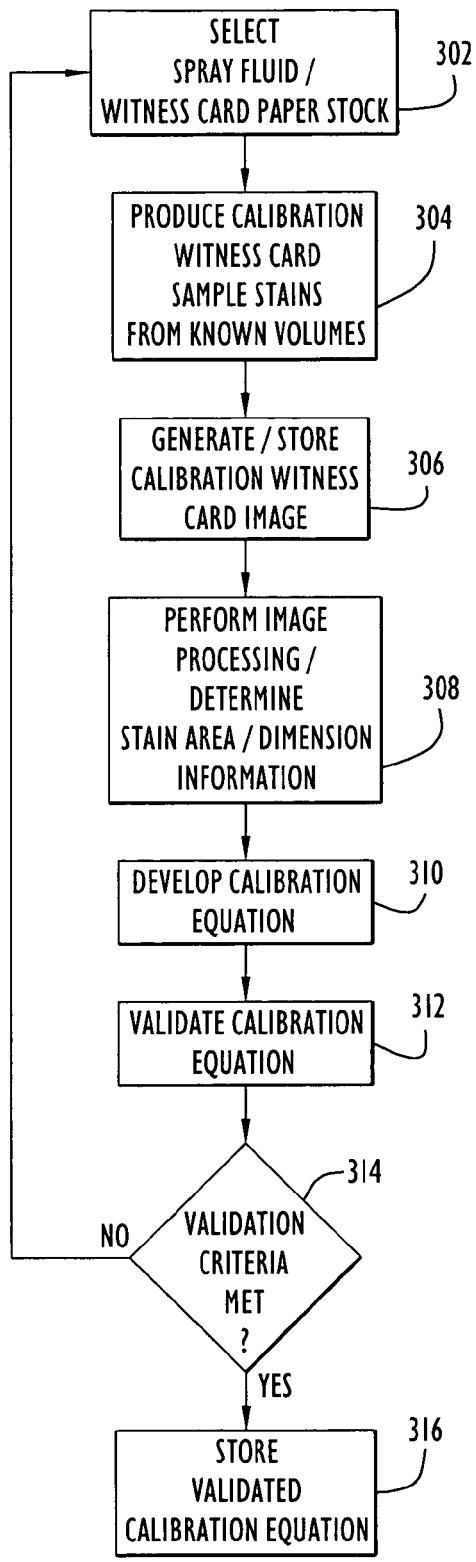
FIG. 3 is a process flow diagram depicting the development of calibration equations used to calibrate a spray performance analysis system in accordance with an exemplary embodiment of the present invention.

FIG. 3 is a process flow diagram depicting the development of calibration equations used to calibrate a spray performance analysis system in accordance with an exemplary embodiment of the present invention. As shown in FIG. 3, a spray fluid and witness card paper stock is selected, at step 302, and calibration witness card sample stains are produced, at step 304, upon the selected paper stock with known volumes of the selected fluid. Next, at step 306, the calibration witness card is scanned by scanner unit 102 (See FIG. 1) to produce an electronic image containing images of the calibration witness card stains. Image processing of the respective stain images is performed, at step 308, by image analysis unit 104 to determine stain area and/or dimension measurements of the sample stains. Examples of such dimension measurements may include a diameter of an identified stain, a radius of an identified stain, and a circumference of an identified stain. Stain area and/or dimension measurement information and droplet volume information is passed to calibration unit 106 to develop, at step 310, a calibration equation, or set of linear and/or non-linear equations, using conventional techniques capable of approximating droplet volume as a function of droplet stain area and/or dimension measurements. The generated calibration equation is validated, at step 312, by calculating stain volume approximations for each of the calibration droplets based upon the measured calibration stain measurements. If the approximated volumes are determined, at step 314, to be within a predetermined percentage error of the known droplet volumes, the generated calibration equation information is stored, at step 316, for later access by the spray performance analysis system statistics unit 108. If the approximated volumes are determined, at step 314, to not be within the predetermined percentage error of the known droplet volumes, the calibration process described above is iterated or repeated until a set of validated calibration equations is achieved.

In selecting a witness card paper stock, at step 302, a variety of commercially available papers are preferably assessed, in order to limit paper speckle and paper imperfections in the scanned images. As described above, a preferred witness card paper for use with the spray performance analysis system of the present invention is sold as 52 lb Epson, single side glossy photo paper, stock number S041649. Preferably, the witness card paper stock used for calibration witness cards and the witness card paper stock used for as-sprayed witness cards are selected from the same manufactured batch. In this manner, the risk of introducing error due to differences in the paper stock used for calibration and the paper stock used for as-sprayed analysis is mitigated.

When producing calibration witness card sample stains, at step 304, droplets may be deposited upon the image side of the paper stock and, except for a ¼" area around each edge, the image side must be kept very clean and not be touched by hands. Calibration cards with stains produced by known volumes of fluid may be produced using a wide variety of conventional laboratory techniques related to accurately weighing, measuring and handling small laboratory samples. Preferable, however, for most drop masses each individual calibration stain is produced upon a very small piece (0.5 inch square or less) of paper stock of known weight. After deposition of a droplet, the paper square is again weighed to obtain a combined weight of the paper and droplet. The mass of the deposited droplet may then obtained by subtracting the known weight of the paper from the known weight of the paper/droplet combination. For very small stains, multiple droplets are deposited on a paper square and the end result is divided by the number of drops. Preferably, the scale or balance used for measuring supports measurements with an accuracy of 1 µg (i.e., 0.001 mg), with a standard deviation of less than or equal to 1 µg and linear characteristics less than or equal to ±4 µg. A commercially available scale that meets these characteristics is sold commercially as the Sartorius Micro model MC5. Once a set of sample stains is produced that represents a wide range of potential spray droplet sizes, individual stain samples may be mounted as a matrix upon a single witness card in preparation for scanning the sample stains into a single calibration witness card scanned image.

In generating a calibration witness card image, at step 306, the matrix of stains on pieces of witness stock is preferably scanned using the same commercially available scanner that will be used to scan as-sprayed witness cards. Further, the scanner is preferably configured in the same manner for scanning a calibration witness card as the scanner will be configured for use in scanning as-sprayed witness cards. Three commercially available scanners found acceptable for use in the spray performance analysis system of the present invention are the Hewlett Packard model 4400C, the Hewlett Packard model 3670, and the Canon Canoscan LiDE30. However, of these three scanners, the Hewlett Packard model 3670 is preferred. Table 1, below, presents configuration parameters found to be appropriate for configuring each of the respective scanners for use in the present invention.

TABLE 1

Setting Scanner Parameters a) Scanner: HP model 4400C

| Scan type | | 8 bit color |
|---|---|---|
| Resolution | | 600 dpi (42.3 µm pixel size) |
| Color | Hue | 80% Red, 0% Yellow |
| | Saturation | 150% |
| Exposure | Highlights | 225 |
| | Shadows | 0 |
| | Midtones | 2.2 | b) Scanner: HP model 3670

| Resize Scale | | 100% |
|---|---|---|
| Resize Units | | inches |
| Resolution | | 600 dpi (42.3 µm pixel size) |
| Color | Hue | Red: x = 60, y = −60; |
| | | Blue: x = 80, y = −40; |
| | Intensity | 150% |
| | Color | Original color |
| | Mirror | Non-invert |
| Lighten/ | Highlights | 225 |
| Darken | Shadows | 0 |
| | Midtones | 2.2 |

TABLE 1-continued

Setting Scanner Parameters

| | | |
|---|---|---|
| | White Lvl | 255 |
| | Black Lvl | 0 |
| c) Scanner: Canon CanoScan LiDE 30 Advanced Mode | | |
| Main Settings | Scan type Resolution | 8 bit grayscale 600 dpi (42.3 μm pixel size) Deselect Descreen Deselect Unsharp Mask Reduce dust & scratches - none |
| Settings | Preferences | Deselect auto cropping Deselect auto tone Deselect remove white borders |

In configuring a scanner for use within the spray performance analysis system of the present invention, it is important to control image parameters and to not allow scanner level filtering. Such parameters can affect the size of stains in the scanned images, especially for very small stains.

Depending on the scanner software it may be possible to bias the scanner color parameters in the direction of the color of a dye included within the sprayed fluid. For example, if the sprayed fluid included a red dye, the scanner color hue can be biased in the red direction. Such a scanner color bias is indicated in Table 1 for the BP model 4400C and the HP model 3670 scanners. Biasing the scanner color setup in the direction of the chemical color has the effect of making very small stains larger. This improves the accuracy in converting very small stains to drop diameters and the detection of drops approaching 100 μm in diameter. For example, stain areas improve better than 15% for drop diameters of 600 μm and this improvement is better than 40% for drop diameters of 300 μm. As drop diameters approach 100 μm, biased color scanning is preferably used, because detecting the corresponding stains after grayscale scanning is problematic. Stain size and threshold of detection may vary based upon the chemical coloring used. One dye that has demonstrated good results when used with TMeS is commercially available as red 26 dye, also known as oil red EGN (CAS #4477-79-6), added in the amount of 1 gram per liter of TMeS fluid. If color biasing is used, as described above, and a color witness card image is produced, the color image is preferably converted to an 8-bit grayscale image and saved as a .BMP file with 256 levels of gray-scale and a resolution of 42.3 μm per pixel. The example, above, is exemplary only. The present invention is not limited to the use of any particular spray/dye materials, scanner hardware, color bias, color bias control parameters, processing technique and/or storage resolution/formats. Any appropriate combination of spray/dye materials, scanner hardware, color bias, color bias control parameters, processing technique and/or storage resolution/formats may be used.

Biased color scanning requires the use of additional scanner setup parameters as indicated above, and may increase the non-linear nature of a calibration equation developed to approximate the calibration sample results; however, color biasing may be used to improve stain detection under certain conditions. The added considerations associated with the use of color biasing are typically weighed against the benefits that may be obtained from the use of color biasing. If the as-sprayed witness cards are expected to contain few small stains, there may be little benefit to the use of color biasing, since the mass contribution of these very small stains to sprayed density and MMD may not degrade the percentage accuracy of the spray performance assessment process.

Referring again to FIG. 3., image processing performed at step 308 by calibration image analysis unit 104 (FIG. 1) to determine stain image parameters can be performed by any commercially available image processing system. One commercially available image processing system capable supporting analysis of calibration and as-sprayed stain images is marketed by Coreco Imaging Inc. under the name of Sherlock™ 6.1. In one exemplary embodiment of the present invention, calibration image analysis unit 104 includes in-line scripts executed within the Sherlock 6.1 image processing environment to isolate stains from background and determine stain areas from the gray-scale .BMP image files.

Optionally, calibration image analysis unit 104 may include a calibration analysis script that allows a user to manually identify a calibration stain or group of stains by moving a box around the stain and sizing the box, by grabbing and dragging one or more edges of the box, until the box encompasses the stain(s) with no other artifacts inside the box.

Within the sized box, the calibration analysis script uses conventional image processing techniques supported by the image processing environment (e.g., Sherlock 6.1) to resolve pixel intensities to a gray scale accuracy of 1 part in 256 and spatially resolves each pixel to a spatial resolution of 42.3 μm per pixel. Based upon a pixel intensity threshold value, the calibration analysis script may produce a binary image (i.e., black and white, without grayscale) of the stain in which all pixels with a grayscale value above the user-defined threshold are set to black and pixels with a grayscale value below the user-defined threshold are set to white, or the converse. The image preprocessing parameters—threshold, gain, offset and filtering are preprogrammed in order to control the influence of paper speckle and/or paper imperfections and to control stain size and stain merging. The image analysis script then uses a looped connectivity algorithm to sum the number of pixels within each stain. This pixel count defines the area of the identified stain.

In one exemplary embodiment, the pixel count is multiplied by the pixel resolution squared (e.g., 42.3 μm per pixel) to determine the area of the identified stain. By assuming that the stain is substantially circular, a stain diameter may be determined based upon the approximated stain area. For example, each stain area determined by the calibration analysis script may be stored within a designate cell within a Microsoft Excel spreadsheet. By assuming that the stain is substantially circular, macro scripts included within the Excel spreadsheet may use conventional translation techniques to translate each stain area into a stain diameter. Further, based upon user input, each stored stain area may be associated with a specific calibration witness card stain (e.g., sample #1, sample #2, etc.). In this manner a calibration data file may be created containing an ordered list of stain areas that can be matched by a user to known droplet masses. Preferably, the calibration data file is named in a manner that identifies the information contained within as scanned calibration witness card image information and associates the information with a specific calibration witness card (e.g., Stain_Calib_1). Further, the file preferably includes fields, or cells, that contain the identity (e.g., TMeS) and/or characteristics of the fluid (e.g., stain used, viscosity of fluid, temperature of fluid, etc.) used to create the witness card and/or conditions related to the operational environment (e.g., ambient temperature, humidity, etc.) in which the witness card was created.

Referring again to FIG. 3, scanned calibration witness card stain information produced, at step 308, by calibration image analysis unit 104, as described above, is supplied, at step 310, to calibration unit 106. In one exemplary embodiment of the present invention, calibration unit 106 includes a Microsoft Excel spreadsheet containing an embedded macro that allows a user to identify a calibration data file, as described above, and relate each stain area stored within the calibration data file with a user provided droplet mass, determined as described above with respect to step 304.

In one exemplary embodiment, the embedded macro assumes that each droplet that forms a calibration stain is a sphere. Based upon the known volume of each calibration stain droplet, as described above with respect to step 304, the macro determines an approximation for the diameter of the droplet that formed each calibration stain. The macro correlates the measured calibration drop masses to their respective stain diameters and uses conventional techniques to develop a set of polynomial equations that model the observed relationship between a droplet mass and the diameter of the stain produced by the droplet upon the witness card. In this manner, a set of polynomial equations is developed that can be used to approximate as-sprayed droplet diameters as a function of as-sprayed witness card stain diameters. The observed droplet stain to droplet mass relationship may be modeled by any number of polynomial equations and/or other types of equations and/or combinations of linear/non-linear equations in order to achieve a close fit for various ranges of stain droplet mass sizes.

For example, a set of two polynomial equations may be developed using conventional techniques to model an observed droplet stain to droplet mass relationship. In such an example, stain diameters larger than a defined threshold stain area value may be fitted to a $4^{th}$ order polynomial with zero offset. Stain diameters equal to or smaller than this critical stain area may be fitted to a $3^{rd}$ order polynomial, with no zero offset. The threshold stain area may be statically or dynamically determined either manually by the user or automatically by the macro itself and is referred to as the Poly Cross-Over Stain Area, or PCOSA. A set of two polynomial equation, as described above, has been shown to give best conversion accuracy across the drop size range of interest using a PCOSA value of 160 pixels, which translates into a drop diameter of 600 μm.

Preferably, the coefficients associated with the $4^{th}$ order polynomial with zero offset and the $3^{rd}$ order polynomial with no zero offset are stored within a file for future use in processing as-sprayed calibration cards. For example, such a file may be named WC_Stat_Template_*.xls, where * is a user defined code tied to a unique test. Such a code may be used to identify the file as associated with a particular chemical and stain calibration. In addition to storing the polynomial coefficients and PCOSA, the first sheet in WC_Stat_Template_*.xls, preferably includes user specific information, sprayed fluid chemical name and sprayed fluid characteristics, such as temperature, viscosity, density, etc. Such a calibration data file may be used to accurately approximate as-sprayed witness droplet masses based upon as-sprayed witness card stain dimension/area information, as described with respect to FIG. 4, below.

Referring again to FIG. 3, a set of calibration equations is validated, at step 312, in order to verify that the calibration equations adequately model the observed droplet mass/stain diameter relationship represented by the processed calibration witness card. For example, the stored 3rd order and 4th order polynomial equation coefficients and PCOSA value may be used to convert stored calibration witness card stain area/stain diameter information to equivalent drop diameters. These drop diameters may be converted to drop masses and compared with the original drop masses.

Comparison accuracy between measured drop masses and masses calculated from diameter conversion using the best fit polynomial equations is preferably better than 2%, assuming that no measurement errors have been made. For example, mass accuracy of TMeS has been shown to be 1.1% on average, with a standard deviation of 5.8% and with ±9% max error for calibrated drop sizes between 200 μm to 7000 μm diameter. For this calibration example TMeS was thickened to 821 cp by adding ~3% concentration of PMM (polymethyl methacrylate) with molecular weight of 4-5 million. Due to the repeatability and accuracy of the digital image processing process and reasonable repeatability of staining on the preferred paper stock, the accuracy for other chemicals should be the same as demonstrated for TMeS providing the initial calibration witness card droplet mass measurements are accurate to the precision of the recommended scale and chemical staining is homogenous with stable color intensity, as described above.

Referring again to FIG. 3, if a comparison, at step 314, indicates that the calculated masses do not agree within a predetermined accuracy level (e.g., 10% of the actual droplet masses), all or portion of the calibration process should be repeated. For $R^2$~<0.99, where R is the standard Pearson correlation coefficient, processing is preferably repeated from step 304, paying particular attention to scale calibration and methodology. For $R^2$~$\geq$0.99, remove outliers from the calibration witness card data set and selectively repeat the calibration process from step 310. Removal and replacement of outlier values in such a manner allows a more accurate set of calibration equations to be generated at step 310.

Figure 4:
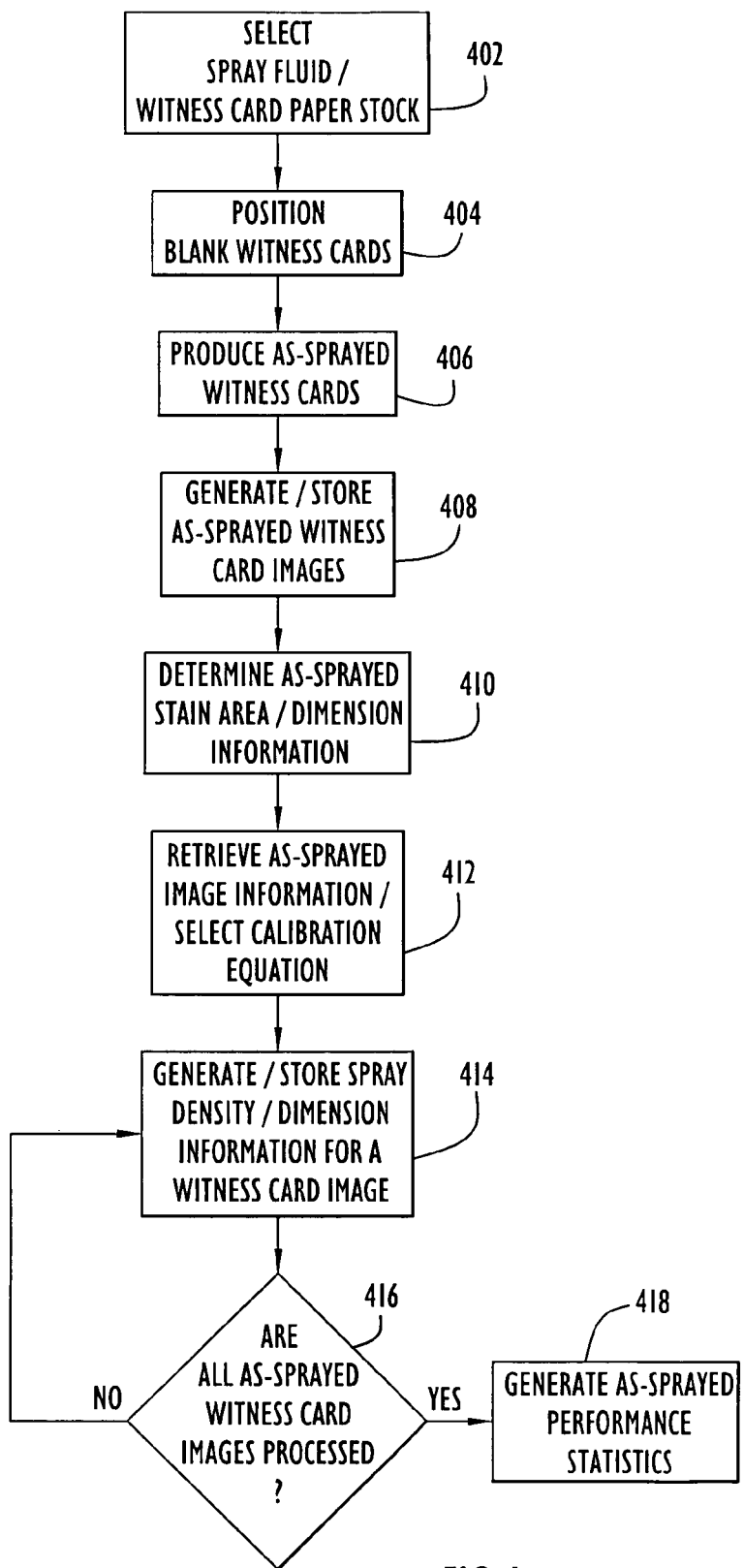
FIG. 4 is a process flow diagram depicting use of the spray performance analysis system of FIG. 1 to generate as-sprayed performance statistics in accordance with an exemplary embodiment of the present invention.

FIG. 4 is a process flow diagram depicting use of the spray performance analysis system of FIG. 1 to generate as-sprayed performance statistics in accordance with an exemplary embodiment of the present invention. As shown in FIG. 4, a spray fluid and witness card paper stock is selected, at step 402, witness cards are positioned, at step 404, throughout an area to be sprayed and as-sprayed witness card stains are produced, at step 406, as a result of spraying the test area with a spray device in a prescribed manner using the selected fluid. For example, the manner of spraying is typically representative of a proposed agricultural, military, industrial or other use, as described above.

Next, at step 408, the as-sprayed witness cards are scanned by scanner unit 102 (See FIG. 1) to produce an electronic image for each as-sprayed card containing images of the respective as-sprayed witness card stains. Image processing of the respective stain images is performed, at step 410, by WC image analysis unit 105 to identify stains within the as-sprayed witness card image that exceed a pre-determined threshold and to determine an approximate area and/or dimension of each detected stain. Examples of such dimension measurements may include a diameter of an identified stain, a radius of an identified stain, and a circumference of an identified stain. Preferably, such as-sprayed witness card stain area and/or dimension information is stored in a manner that associates the witness card with a unique test (e.g., a unique test identifier, etc.).

Step 410, as performed by WC image analysis unit 105 includes in-line scripts executed within the Sherlock 6.1 image processing environment similar to the scripts in the calibration image analysis unit 104 for image preprocessing. However, WC image analysis unit 105 is configured to support automatic image analysis of the sprayed WC's, which may contain many tens of thousands of stains.

At step, 412, statistics unit 108, retrieves as-sprayed witness card stain area measurement and/or dimension information associated with a common test from storage and further retrieves a set of calibration equations for use in approximating the mass of the droplet that produced each identified as-sprayed witness card stain. Next, at step 414, statistics unit 108 generates and stores spray density and droplet mass data for an as-sprayed witness card associated with the selected test. If the statistics unit 108 determines, at step 416, that additional as-sprayed witness card stain area and/or dimension information remains to be processed, step 414 is repeated, otherwise, statistics unit 108 proceeds to generate, at step 418, statistics data that summarizes as-sprayed performance based upon the spray density and droplet mass data generated, at step 414, for each of the respective as-sprayed witness cards. Additional detail related to steps identified in FIG. 4 is provided below.

In selecting a witness card paper stock, at step 402, the same paper stock selected for use in the calibration process, described above, should be used. Preferably, the paper will come from the same manufacturing batch as the card stock used in the calibration process. Witness card paper stock image side should be clean, dry and surface to be stained untouched, except for a ¼" area around each edge. Any marks or smudges will affect stain statistics or will force a reduction in area of the witness card that can be analyzed.

In selecting a spray fluid, at step 402, the same fluid used in the calibration process should be used. Preferably, the fluid will originate from the same batch of fluid chemicals used to perform witness card calibration and to generate the set of calibration equations intended for use in analyzing the as-sprayed witness cards at step 414. If the fluid used to perform calibration is not available, the sprayed fluid should be as close to the calibration fluid as possible. For example, the as-sprayed fluid composition, color intensity, viscosity, and temperature is preferably as close to the calibration fluid as possible.

In accordance with an exemplary embodiment of the present invention, the process flow described with respect to FIG. 4 may be adapted for use with uncalibrated spray fluids. If a set of as-sprayed witness cards has been created using an uncalibrated spray fluid, a default calibration equation may be selected, at step 412. Once the spray fluid has been calibrated, the spray density and dimension information generated, at step 412, and as-sprayed performance statistics generated, at step 418, may be updated to reflect the newly developed spray fluid calibration equation.

Several techniques may be used to mitigate risks associated with different as-sprayed fluid characteristics. For example, sets of calibration equations may be developed for a fluid compound at different fluid temperatures. The generated sets of calibration equation information may be stored and an appropriate set of calibration equations later selected, at step 412, for use based upon the temperature of the as-sprayed fluid at the time that the as-sprayed witness are generated. Optionally, information related to changes in witness card stain diameter as a function of temperature/viscosity may be used to scale the as-sprayed estimates produced by a selected calibration equation to accommodate as-sprayed temperature/viscosity and/or other considerations.

In positioning, at step 404, witness cards within a target spray area, care should be taken to place the witness cards in positions that may capture appropriate spray information. For example, witness cards may be placed at strategically selected and/or evenly spaced locations from a stationary spray distribution point, or a ground zero detonation point, to form one or more representative grids and/or cross-sections of the target area. If the spray device is mobile, witness cards may be placed at strategically selected locations and/or evenly spaced intervals along the spray path. For example, to sample spray performance of a spray device moving along a spray path, a set of witness cards may be positioned along a perpendicular cross-section of the spray path. Such cross-sectional sampling may be established at various points along the spray path to obtain information related to performance of the spray device over time.

In producing as-sprayed witness cards, at step 406, care should be taken to monitor the as-sprayed operational conditions and any deviations from the operational conditions under which the calibration witness card was created should be duly noted. Such notable changes may include, as-sprayed fluid temperature, as sprayed viscosity, color intensity, wind conditions, ambient temperature/humidity, etc. Preferably, the as-sprayed operational conditions can be matched at step 412 with a set of calibration equations based upon calibration witness card data produced under the same operational conditions. This matching may be conveniently done post-spraying as noted above.

In producing as-sprayed witness card images, at step 408, the same scanning unit 102 (FIG. 1) used to create calibration witness card images is preferably used. Further, scanning parameters associated with the scanner are preferably unchanged from the parameters used to create the calibration witness card images used to generate the set(s) of calibration equations that are used at step 414 to process the as-sprayed witness card stain information. Preferably, 90-95% of each witness card is scanned and each image saved to a separate gray scale .BMP file with 256 levels of gray-scale and a resolution of 42.3 μm per pixel. Further, each file is preferably identified with a unique identifier that associates the image file with the as-sprayed witness card from which the scanned image was produced. If color biasing was used during, the color image should be converted to a gray-scale .BMP, as described above.

Optionally, color images may be stored and processed by units 104 and 105. In order to support color image processing, the image processing environment must support colored images and the file sizes associated with witness card color images. Color images may be four times the size of gray scale images. For example, a 5"×8" WC will create a 70+ MB color image .BMP file compared to a 17 MB gray scale .BMP file.

Optionally, other file types than .BMP may be used, as supported by the image processing environment and image quality requirements. Some file types, such as JPEG, are preferably not used because JPEG compression may degrade the image and adversely effect generated results.

In analyzing as-sprayed witness card images to produce, at step 410, as-sprayed stain area/dimension information, WC image analysis unit 105 (FIG. 1) control parameters are preferably configured to mirror the same parameters used during the calibration process performed by unit 104 (FIG. 1) at step 308 (FIG. 3). For example, WC image analysis unit 105 may include an as-sprayed analysis script that configures image analysis unit 105 with the same control parameters used by the unit 104 calibration analysis script, described above. Generated as-sprayed stain area and stain dimension information (e.g., diameter, radius, circumference, etc.) is stored for subsequent access by statistics unit 108 at steps 412-414.

In one embodiment, image analysis unit 104 determines as-sprayed stain area and/or dimension information for each as-sprayed stain detected within an as-sprayed witness card image and stores the determined information within uniquely identified cells within a Microsoft Excel spreadsheet. In this manner, an as-sprayed witness card data file is created containing an ordered list of stain areas and/or dimension information. Preferably the file is named in a manner that identifies the information contained within as-sprayed witness card image information and identifies the information with a specific as-sprayed witness card (e.g., Stain_Data_WC_1, Stain_Data_WC_2, etc.). Further, the file my include fields, or cells, that associate the information with a specific test, such as a unique test identifier, a test date/time, the identity (e.g., TMeS) and/or characteristics of the fluid used to create the witness card (e.g., stain/color intensity used, viscosity of fluid, temperature of fluid, etc.) and/or conditions related to the operational environment in which the witness card was created (e.g., ambient temperature, humidity, etc.) As described with respect to the calibration process above, by assuming that the stain is substantially circular, macro scripts included within the Excel spreadsheet may use conventional translation techniques to translate each stain area into a stain diameter, radius and/or stain circumference.

As-sprayed witness card image analysis performed by WC image analysis unit 105 at step 410 may be performed in a manner very similar to the image analysis performed upon calibration witness card images described above. However, for any WC's containing a reasonable number of stains, an automatic process is desired or required. For example, as the number of stains exceeds many dozen, a manual approach of selecting stains becomes impractical and as the number grows to many hundreds, a manual approach becomes impossible.

Embodied in the WC image analysis unit 105 is an automatic process for stain analysis. After the image is preprocessed to mirror the calibration image setup, WC image analysis unit 105 analyzes stains within the WC sample space boundary, which is typically set ¼" from each edge.

During this automated process, stains on the sample space boundary are eliminated and the value for the witness card sample area is updated to reflect the area removed from the sample area associated with the eliminated stains. In general, if boundary stains are included, step 418 statistics will be skewed or in will be error because boundary stains would have been artificially reduced in size. Rejecting these boundary stains is generally necessary but not sufficient because the density statistic would be in error. Thus it is necessary to eliminate boundary stains and to correct (reduce) the sample space area proportionately. There is one special case in which including boundary stains may be desired. This special case occurs when stains are extremely small and very dense to the point where a significant proportion of the stains merge. To handle this case a means may be provided to modify the in-line script prior to image analysis.

An as-sprayed analysis script may set image processing environment control parameters to a set identical to those used in the calibration process, described above, and may control user access to the image processing environment. For example, the user may be restricted from changing one or more pre-set image processing environment control parameters and/or restricted to the use of only a limited set of image processing environment options. By way of a second example, a user may be limited to identifying the location of a set of as-sprayed witness card images, and for each image manually identify a witness card image scan area by grabbing and dragging one or more edges of an image scan area box, until the box encompasses a different percentage of the as-sprayed witness card scanned image area.

Within the witness card image scan area box, the as-sprayed analysis script uses conventional image processing techniques supported by the image processing environment (e.g., Sherlock 6.1) to resolve pixel intensities to a gray scale accuracy of 1 part in 256 and spatially resolves each pixel to a spatial resolution of 42.3 µm per pixel. Optionally, witness card image pixels may be rescaled by selecting different scanning parameters. Such rescaling may be used to increase or decrease contrast between stain images and the witness card background speckle. Once stain contrast acceptable to the user is obtained, the WC analysis script may produce a binary image (i.e., black and white, without grayscale) of the as-sprayed witness card based upon the user-defined threshold value, as described above, in which all pixels with a grayscale value above the user-defined threshold is set to black and pixels with a grayscale value below the user-defined threshold is set to white. This relationship may be reversed, but must be consistent with the calibration process. The pixel intensity threshold value may be automatically selected or user-defined (e.g., dynamically set by the user during the calibration process) in order to control the influence of paper speckle and/or paper imperfections, but this value must be the same between units 104 and 105. The as-sprayed analysis script may then use conventional image processing capabilities provided by the image processing environment to locate and identify stains within a witness card image. For example, a looped connectivity algorithm may be used to sum the number of pixels within an identified stain, or blob, in the processed image and/or to collect stain statistics. In performing such analysis, the as-sprayed processing script criteria may operate to detect and analyze stains, or blobs, in accordance a set of controlling definitions, or guidance parameters, which may include:

a. Sample Space: The user defined area witness card image scan area. The sample space is preferably smaller than the witness card image to avoid statistic skewing due to lack of stains around the card edges. The witness card image scan area may be defined by dragging a box to include up to preferably 95% of the witness card image area, thereby providing a border around the image card to allow for physical handling of the card without affecting the witness card analysis process. The sample space is preferably resized or moved if there are 1) non-stain artifacts within the sample space or 2) the sample space is too close to a card edge. The as-sprayed processing script may identify and process only those stains entirely within the sample space.
   b. Stain: Any connected group of pixels above a grayscale threshold.
   c. Separate Stains: Two closely spaced stains must be separated by at least one pixel below the grayscale threshold to be considered separate stains.
   d. Merged Stains: Stains that touch and as such are classified as a single stain. This characteristic does not affect reported total area of stains in the sample space but could affect other statistical parameters such as average size and largest stain, depending on the number of occurrences and specific values. The image processing environment may present a visual image of identified witness card stains in order to provide the user with visual feedback regarding image processing interpretation of a witness card image (e.g., number, number of merged stains, etc.) based upon the current control parameters (e.g., rescaling values used, if any, threshold pixel value, etc.) For example, merged stains may be identified with halos inserted by the as-sprayed image analysis script into the image interpretation presented to the user.

e. Chemical stringers: Stringers are formed as a result of a dynamic process or inappropriate mechanical sprayer setup and/or spraying protocol in which a liquid mass resembling a piece of string hits the WC creating a line stain. These stains, reported in terms of pixel areas, will be interpreted as circles with calculated pseudo diameters. Stringers should be avoided and in fact seldom occur with a homogeneous chemical mix and good spraying technique.

f. Boundary Stains: Stains on the sample space boundary. The as-sprayed image analysis script may be set up to ignore stains that are not completely within the sample space. Thus, the statistics are not skewed by stains that appear to be split by the demarcation boundary that defines the sample space on the card. The sample space area (as used in calculation of drop concentration) is corrected (reduced in proportion) for the absence of any omitted boundary stains.

In one exemplary embodiment, the pixel count is multiplied by the pixel resolution squared (e.g., 42.3 μm per pixel) to determine the area of an identified stain. By assuming that the stain is substantially circular, a stain diameter may be determined based upon the approximated stain area approximated by the image analysis described above. Each stain area determined by the as-sprayed analysis script may be stored within a designated cell within an as-sprayed witness card Microsoft Excel spreadsheet. By assuming that the stain is substantially circular, macro scripts included within the Excel spreadsheet may use conventional translation techniques to translate each stain area into a stain diameter. Given the large number of stains that may be detected within an as-sprayed witness card image, stain information may be assigned a unique identifier, automatically by the as-sprayed analysis script (e.g., stain#1, . . . stain #N, etc.). In this manner, an as-sprayed data file is created containing an ordered list of stain areas and/or dimension information. Preferably the file is named in a manner that identifies the information with a specific witness card (e.g., Stain_data_WC_1). Preferably, the file should include fields, or cells, that contain the identity (e.g., TMeS) and/or characteristics of the fluid used to create the as-sprayed witness card (e.g., stain used, viscosity of fluid, temperature of fluid, etc.) and/or conditions related to the operational environment in which the witness card was created (e.g., ambient temperature, humidity, etc.)

Information generated and stored by the as-sprayed image analysis script within a file or other information store, such as a database, may include:

1. Name of the witness card image processed
2. Number of stains omitted (less than minimum size specified)
3. Number of stains found
4. Total area of stains in sample space
5. Corrected Sample Space area
6. Sample Space Correction factor
7. % ratio of stains in sample space to sample space area
8. Stain minimum size
9. Smallest and largest stains found
10. Average stain size
11. Total stain area
12. Pixel resolution
13. Program settings used to analyze the image
14. Critical Definitions (see above a to f list)
15. An ordered list of all stains from smallest to largest, but limited to stains larger than a minimum size set by a user or within the as-sprayed processing script. (e.g., greater than 106 μm in diameter)

The above items may be contained in documentation that is automatically prepared to be recorded to files, as follows:

1. Text file containing above items 1-14 (quick-look summary)
2. BMP image of sample space (17 MB)
3. Excel text file containing above items 1-13 and 15, above.

Recording the text file and BMP image to disk is optional with the "record" condition being preset before image processing. The most important and complete record is the Excel file that contains the list of stain areas. This information is used by statistics unit 108 (FIG. 1) to calculate spray density and mass median diameter information.

Referring again to FIG. 4, depending upon the storage approach used, statistics unit 108 (FIG. 1) may retrieve stored as-sprayed witness card stain area/dimension information and may retrieve a set of calibration equations, at step 412, based upon a common file naming convention and/or based upon test description and/or operational environment information associated with a selected test. For example, if as-sprayed witness card information and calibration equation information is stored in separate Excel files, as described above, using a common naming convention, the statistics unit may retrieve data files and calibration information for a test based upon the common naming convention. Further, if multiple sets of calibrations are available for selection, statistics unit 108 may choose a set of calibration equations based upon as-sprayed operational information associated with the test.

Next, at step 414, statistics unit 108 generates and stores spray density and droplet mass data for an as-sprayed witness card associated with the selected test. If the statistics unit 108 determines, at step 416, that additional as-sprayed witness card stain area measurement and/or dimension information remains to be processed, step 414 is repeated, otherwise, statistics unit 108 proceeds to generate, at step 418, statistics data that summarizes as-sprayed performance based upon the spray density and droplet mass data generated, at step 414, for each of the respective as-sprayed witness cards.

In one exemplary embodiment, statistics for a particular set of witness cards are developed in an Excel statistics summary spreadsheet named W_Stat_Template_*.xls, where * is a user defined identifier tied to user calibration and test records. This file, described with respect to FIG. 3, block 310, is populated during the calibration process with the coefficients of the generated calibration polynomial equations and sprayed fluid related information. The WC_Stat_Template_*.xls file created for each test may be based upon a master template stored in a commonly accessible file directory as Stat_Template.xls. The statistics summary spreadsheet may include a statistics summary worksheet that contains general information related to the test (e.g., test name, fluid sprayed, fluid density, fluid temperature, fluid viscosity, stain/stain intensity, etc.) and may include a witness card summary that includes a single row for each witness card populated with summary statistics related to the witness card.

Preferably, the WC_Stat_Template_*.xls further includes a witness card worksheet for each witness card associated with the test. To add more sheets to WC_Stat_Template_*.xls, new blank worksheets may be created and cells may be copied from the last witness card worksheet into the new witness card worksheets, being careful to absolutely register the cells. For each new witness card worksheet added, a witness card line may be added to the witness card summary, described above, to automatically accept witness card specific statistics data.

A unique copy of the WC_Stat_Template_*.xls may be created for each test run or group of witness cards. Each witness card worksheet within the statistics summary spreadsheet may contain instructions on loading the sheet with data from the respective as-sprayed witness card data files (e.g., Test1_Stain_data_WC_1) created by image analysis unit 104, as described with respect to FIG. 4, at step 410, containing an ordered list of stain areas and/or dimension information.

Upon loading as-sprayed witness card data file information into the respective statistics summary worksheets, a statistics unit 108 (FIG. 1) macro embedded within the statistics summary spreadsheet may be invoked to process the respective witness card worksheets. Statistics unit 104 may use such a macro to calculate a stain diameter for each witness card stain area listed, based on the presumption that each stain is a circle. Further, the statistics unit macro may determine a drop diameter for each stain diameter using the calibration equations imbedded in the statistics summary spreadsheet, as described above.

The statistics unit macro may calculate the mass of a droplet based upon the determined drop diameter and an assumption that each drop is a sphere. Calculating spray density, MMD (mass median diameter) and mass surface density for the witness card completes the analysis process. The mass surface density is calculated as the sum of all calculated drop masses in the witness card sample space analyzed, divided by the corrected sample space area. MMD is calculated based on the standard industry definition as described above.

After applying the imbedded statistics unit macro to a witness card worksheet, key statistical information is automatically transferred to a row within statistics summary worksheet associated with the witness card, as described above. When all witness card worksheets have been processed and the summary sheet contains statistical data for each as-sprayed witness card, group summary statistics, such as averages of the statistics generated for individual witness card, may be generated and included within the statistics summary worksheet.

It may be appreciated that the embodiments described above and illustrated in the drawings represent only a few of the many ways of implementing and applying image processing techniques to perform statistical analysis of as-sprayed witness cards to assess performance of a spray device. The present invention is not limited to the specific embodiments disclosed herein and variations of the method and apparatus described here may be used to perform witness card statistical analysis using image processing techniques to assess the as-sprayed performance of any spray device used in any operational environment.

The spray performance analysis system described here can be implemented in any number of units, or modules, and is not limited to any specific software module architecture. Each module can be implemented in any number of ways and are not limited in implementation to execute process flows precisely as described above. The spray performance analysis system described above and illustrated in the flow charts and diagrams may be modified in any manner that accomplishes the functions described herein. It is to be understood that various functions of the spray performance analysis system may be distributed in any manner among any quantity (e.g., one or more) of hardware and/or software modules or units, computer or processing systems or circuitry.

The spray performance analysis system of the present invention is not limited to use in the analysis of fluid sprays, but may be used to assess the distribution of any fluid and/or particles of fluid and solid matter impacts upon witness cards as the result of any energizing force, including explosions, wind and/or any other natural and/or man-made discharge.

Further, WC's are not limited to paper. Witness cards may include any surface that may be used to generate and image representing stains, or marks, upon the witness card surface. Such surfaces may include, but are not limited to, photographic plates, photo sensitive media, the surface of an electronic scanner and planar surfaces made of any material (e.g., transparent plastic/glass, opaque plastic, wood, metal, etc.). Stain materials are not limited to fluids and may include solid particles, energy particles (e.g., electron beams, photons) and any other material capable of impacting a witness card surface in a manner that leaves an indication that an impact has occurred.

Nothing in this disclosure should be interpreted that the calibration relationship approximating an observed relationship between stain area/dimension information and the mass of a droplet that formed the stain is limited to being described using two equations and/or limited to polynomial equations and/or to a set of 3rd and 4th order polynomial equations. Calibration equations may include any number, type (e.g., linear, non-linear, etc.) and/or combination of equations. Sets of calibration equations may include any number of equations, and/or any type of equation and/or any combination of different types of equations that can accurately model any portion of a relationship between stain area/dimension information and the mass of a droplet that formed the stain.

Changes in witness card stain diameters as a function of temperature/viscosity may be modeled using any combination of equations and in an exemplary embodiment may be used to adjust a set of calibration equations to accommodate differences between a calibration environment in which a set of calibration equations are developed and an as-sprayed operational environment. Such calibration equation adjustments may be stored in any manner and associated with a set of determined calibration equations in any manner.

The spray performance analysis system may be executed within any available operating system that supports a command line and/or graphical user interface (e.g., Windows, OS/2, Unix, Linux, DOS, etc.). The spray performance analysis system may be installed and executed on any operating/hardware platform and may be performed on any quantity of processors within the an executing system or device. The analysis system may be configured as a portable or stationary unit.

It is to be understood that the spray performance analysis system may be implemented in any desired computer language and/or combination of computer languages, and could be developed by one of ordinary skill in the computer and/or programming arts based on the functional description contained herein and the flow charts illustrated in the drawings. Further, spray performance analysis system units may include commercially available components tailored in any manner to implement functions performed by the spray performance analysis system described here. Moreover, the spray performance analysis system software may be available or distributed via any suitable medium (e.g., stored on devices such as CD-ROM and diskette, downloaded from the Internet or other network (e.g., via packets and/or carrier signals), downloaded from a bulletin board (e.g., via carrier signals), or other conventional distribution mechanisms).

The spray performance analysis system may accommodate any quantity and any type of data files and/or databases or other structures and may store witness card stain information, summary statistics and/or any other information in any desired file and/or database format (e.g., ASCII, binary, plain text, or other file/directory service and/or database format, etc.). Further, any references herein to software, or commercially available applications, performing various functions generally refer to processors performing those functions under software control. Such processors may alternatively be implemented by hardware or other processing circuitry. The various functions of the spray performance analysis system may be distributed in any manner among any quantity (e.g., one or more) of hardware and/or software modules or units. Processing systems or circuitry, may be disposed locally or remotely of each other and communicate via any suitable communications medium (e.g., hardwire, wireless, etc.). The software and/or processes described above and illustrated in the flow charts and diagrams may be modified in any manner that accomplishes the functions described herein.

From the foregoing description it may be appreciated that the present invention includes a method and apparatus for witness card statistical analysis using image processing techniques that allows as-sprayed performance statistics for a spray device to be quickly and efficiently generated based upon a comprehensive analysis of as-sprayed witness card stains.

The spray performance analysis technique may be executed without the use of WC's by exposing the scanner directly to the spray environment. In this embodiment, the scanner would produce an image of the sprayed condition directly from the scanner bed. Such a concept leads directly to a unit that, when combined with an integral image processing computer containing units 105 and 108, would produce a near instantaneous output from a spray test. Such an embodiment may include a transparent, disposable covering that protects the scanner bed surface during a spray event and that can be replaced with a clean protective cover prior to each spray event.

Having described preferred embodiments of a method and apparatus for witness card statistical analysis using image processing techniques, it is believed that other modifications, variations and changes may be suggested to those skilled in the art in view of the teachings set forth herein. It is therefore to be understood that all such variations, modifications and changes are believed to fall within the scope of the present invention as defined by the appended claims.

What is claimed is:

1. A system for assessing a spray using image processing techniques to analyze a scan image of an as-sprayed witness card, wherein the as-sprayed witness card includes a fixed pattern of stains as a result of being sprayed with drops of a selected fluid, the system comprising:
    a scanner unit to generate a scan image of a calibration witness card and a scan image of at least one as-sprayed witness card, wherein the calibration witness card includes a plurality of stains, each stain created with a known volume of the selected fluid;
    an image analysis unit to identify a plurality of stains within a scan image and to determine a value for a selected dimensional characteristic for each identified stain based upon image processing of the scan image;
    a calibration unit to develop a calibration equation based upon values determined for stains identified within the calibration witness card scan image, wherein the calibration equation approximates a relationship between the determined calibration witness card stain values and the respective volumes of the selected fluid that created each respective calibration witness card stain; and
    a statistics unit to determine an as-sprayed drop characteristic based upon a value determined for a stain identified within the as-sprayed witness card scan image and the developed calibration equation.

2. The system of claim 1, wherein the calibration equation includes a non-linear component.

3. The system of claim 1, wherein the calibration equation includes a set of calibration equations.

4. The system of claim 3, wherein the set of calibration equations includes at least one non-linear equation.

5. The system of claim 1, wherein the scanner unit further includes:
    a scan color bias unit to increase the sensitivity of the scanner to at least one selected color.

6. The system of claim 1, wherein the scanner unit further includes:
    an image storage unit that stores a generated scan image.

7. The system of claim 6, wherein the image storage unit is configured to store the scan image as a gray scale image.

8. The system of claim 6, wherein the image storage unit is configured to store the scan image as a color image.

9. The system of claim 6, wherein the image storage unit is configured to store the scan image in one of a file and a database.

10. The system of claim 1, wherein the dimensional characteristic value determined by the image analysis unit for a stain is at least one of:
    an area of an identified stain;
    a diameter of an identified stain;
    a radius of an identified stain; and
    a circumference of an identified stain.

11. The system of claim 1, wherein the image analysis unit further includes:
    a value storage unit to store determined witness card stain values.

12. The system of claim 11, wherein the value storage unit is configured to store values in at least one of a file and a database.

13. The system of claim 1, wherein the calibration unit further includes:
    an equation storage unit to store at least one of a determined equation and a determined equation coefficient.

14. The system of claim 13, wherein the equation storage unit is configured to store determined equations in at least one of a file and a database.

15. The system of claim 1, wherein the as-sprayed characteristic determined by the statistics unit is at least one of:
    an as-sprayed drop diameter;
    an as-sprayed drop volume;
    an as-sprayed drop mass;
    an as-sprayed drop mass median diameter; and
    an as-sprayed spray density.

16. A method for assessing a spray using image processing techniques to analyze a scan image of an as-sprayed witness card, wherein the as-sprayed witness card includes a fixed pattern of stains as a result of being sprayed with drops of a selected fluid, the method comprising:

(a) generating a scan image of a calibration witness card and a scan image of at least one as-sprayed witness card, wherein the calibration witness card includes a plurality of stains, each stain created with a known volume of the selected fluid;

(b) identifying a plurality of stains within a scan image and determining a value for a selected dimensional characteristic for each identified stain based upon image processing of the scan image;

(c) determining a calibration equation based upon values determined for stains identified within the calibration witness card scan image, wherein the calibration equation approximates a relationship between the determined calibration witness card stain values and the respective volumes of the selected fluid that created each respective calibration witness card stain; and (d) determining an as-sprayed drop characteristic based upon a value determined for a stain identified within the as-sprayed witness card scan image and the developed calibration equation.

17. The method of claim 16, wherein the calibration equation includes a non-linear component.

18. The method of claim 16, wherein the calibration equation includes a set of calibration equations.

19. The method of claim 18, wherein the set of calibration equations includes at least one non-linear equation.

20. The method of claim 16, wherein step (a) further includes:
(a.1) increasing the sensitivity of the scanner to at least one selected color.

21. The method of claim 16, wherein step (a) further includes:
(a.1) storing a generated scan image.

22. The method of claim 21, wherein step (a.1) further includes:
(a.1.1) storing a generated scan image as a gray scale image.

23. The method of claim 21, wherein step (a.1) further includes:
(a.1.1) storing a generated scan image as a color image.

24. The method of claim 21, wherein step (a.1) further includes:
(a.1.1) storing a generated scan image in one of a file and a database.

25. The method of claim 16, wherein the determined dimensional characteristic is at least one of:
an area of an identified stain;
a diameter of an identified stain;
a radius of an identified stain; and
a circumference of an identified stain.

26. The method of claim 16, wherein step (b) further includes:
(b.1) storing a determined witness card stain value.

27. The method of claim 26, wherein step (b.1) further includes:
(b.1.1) storing a determined witness card stain value in at least one of a file and a database.

28. The method of claim 16, wherein step (c) further includes:
(c.1) storing at least one of a determined equation and a determined equation coefficient.

29. The method of claim 28, wherein step (c.1) further includes:
(c.1.1) storing at least one of the determined equation and a determined equation coefficient in at least one of a file and a database.

30. The method of claim 16, wherein step (d) the determined as-sprayed characteristic is at least one of:
an as-sprayed drop diameter;
an as-sprayed drop volume;
an as-sprayed drop mass;
an as-sprayed drop mass median diameter; and
an as-sprayed spray density.

31. A program product apparatus having a computer readable medium with computer program logic recorded thereon for assessing a spray using image processing techniques to analyze a scan image of an as-sprayed witness card, wherein the as-sprayed witness card includes a fixed pattern of stains as a result of being sprayed with drops of a selected fluid, said program product apparatus comprising:
a scanner unit to generate a scan image of a calibration witness card and a scan image of at least one as-sprayed witness card, wherein the calibration witness card includes a plurality of stains, each stain created with a known volume of the selected fluid;
an image analysis unit to identify a plurality of stains within a scan image and to determine a value for a selected dimensional characteristic for each identified stain based upon image processing of the scan image;
a calibration unit to develop a calibration equation based upon values determined for stains identified within the calibration witness card scan image, wherein the calibration equation approximates a relationship between the determined calibration witness card stain values and the respective volumes of the selected fluid that created each respective calibration witness card stain; and
a statistics unit to determine an as-sprayed drop characteristic based upon a value determined for a stain identified within the as-sprayed witness card scan image and the developed calibration equation.

32. The program product of claim 31, wherein the calibration equation includes a non-linear component.

33. The program product of claim 31, wherein the calibration equation includes a set of calibration equations.

34. The program product of claim 33, wherein the set of calibration equations includes at least one non-linear equation.

35. The program product of claim 31, wherein the scanner unit further includes:
a scan color bias unit to increase the sensitivity of the scanner to at least one selected color.

36. The program product of claim 31, wherein the scanner unit further includes:
an image storage unit that stores a generated scan image.

37. The program product of claim 36, wherein the image storage unit is configured to store the scan image as a gray scale image.

38. The program product of claim 36, wherein the image storage unit is configured to store the scan image as a color image.

39. The program product of claim 36, wherein the image storage unit is configured to store the scan image in one of a file and a database.

40. The program product of claim 31, wherein the dimensional characteristic value determined by the image analysis unit for a stain is at least one of:
an area of an identified stain;
a diameter of an identified stain;
a radius of an identified stain; and
a circumference of an identified stain.

41. The program product of claim 31, wherein the image analysis unit further includes:

a value storage unit to store determined witness card stain values.

42. The program product of claim 41, wherein the value storage unit is configured to store values in at least one of a file and a database.

43. The program product of claim 31, wherein the calibration unit further includes:
an equation storage unit to store at least one of a determined equation and a determine equation coefficient.

44. The program product of claim 43, wherein the equation storage unit is configured to store determined equations in at least one of a file and a database.

45. The program product of claim 31, wherein the as-sprayed characteristic determined by the statistics unit is at least one of:
an as-sprayed drop diameter;
an as-sprayed drop volume;
an as-sprayed drop mass;
an as-sprayed drop mass median diameter; and
an as-sprayed spray density.

46. A method for calibrating a system for assessing a spray using image processing techniques to analyze a scan image of an as-sprayed witness card, wherein the as-sprayed witness card includes a fixed pattern of stains as a result of being sprayed with drops of a selected fluid, the method comprising:
(a) generating a scan image of a calibration witness card, wherein the calibration witness card includes a plurality of stains, each stain created with a known volume of the selected fluid;
(b) identifying a plurality of stains within the scan image and determining a value for a selected dimensional characteristic for each identified stain based upon image processing of the scan image; and
(c) determining a calibration equation based upon values determined for stains identified within the calibration witness card scan image, wherein the calibration equation approximates a relationship between the determined calibration witness card stain values and the respective volumes of the selected fluid that created each respective calibration witness card stain;
wherein the calibration equation is used for determining an as-sprayed drop characteristic based upon a value determined for a stain identified within the as-sprayed witness card scan image and the developed calibration equation.

47. The method of claim 46, wherein the calibration equation includes a non-linear component.

48. The method of claim 46, wherein the calibration equation includes a set of calibration equations.

49. The method of claim 48, wherein the set of calibration equations includes at least one non-linear equation.

50. The method of claim 46, wherein step (a) further includes:
(a.1) increasing the sensitivity of the scanner to at least one selected color.

51. The method of claim 46, wherein step (a) further includes:
(a.1) storing a generated scan image.

52. The method of claim 51, wherein step (a.1) further includes:
(a.1.1) storing a generated scan image as a gray scale image.

53. The method of claim 51, wherein step (a.1) further includes:
(a.1.1) storing a generated scan image as a color image.

54. The method of claim 51, wherein step (a.1) further includes:
(a.1.1) storing a generated scan image in one of a file and a database.

55. The method of claim 46, wherein the determined dimensional characteristic is at least one of:
an area of an identified stain;
a diameter of an identified stain;
a radius of an identified stain; and
a circumference of an identified stain.

56. The method of claim 46, wherein step (b) further includes:
(b.1) storing a determined witness card stain value.

57. The method of claim 56, wherein step (b.1) further includes:
(b.1.1) storing a determined witness card stain value in at least one of a file and a database.

58. The method of claim 46, wherein step (c) further includes:
(c.1) storing at least one of a determined equation and a determined equation coefficient.

59. The method of claim 58, wherein step (c.1) further includes:
(c.1.1) storing at least one of the determined equation and a determined equation coefficient in at least one of a file and a database.

60. The method of claim 46, wherein step (d) the determined as-sprayed characteristic is at least one of:
an as-sprayed drop diameter;
an as-sprayed drop volume;
an as-sprayed drop mass;
an as-sprayed drop mass median diameter; and
an as-sprayed spray density.

* * * * *